(12) United States Patent
Chinzei

(10) Patent No.: US 7,063,479 B2
(45) Date of Patent: Jun. 20, 2006

(54) LINK MECHANISM OF SURGICAL ROBOT

(75) Inventor: Kiyoyuki Chinzei, Tsukuba (JP)

(73) Assignee: Secretary of Agency of Industrial Science and Technology, Tokyo (JP)

( * ) Notice: Subject to any disclaimer, the term of this patent is extended or adjusted under 35 U.S.C. 154(b) by 0 days.

(21) Appl. No.: 09/749,125

(22) Filed: Dec. 26, 2000

(65) Prior Publication Data

US 2001/0008599 A1    Jul. 19, 2001

(30) Foreign Application Priority Data

Jan. 13, 2000    (JP)    ............................. 2000/004945

(51) Int. Cl.
*F16C 11/06*    (2006.01)
(52) U.S. Cl. ..................... 403/46; 74/490.06; 384/38; 600/424
(58) Field of Classification Search ................ 403/56, 403/63, 122, 128, 131; 384/38, 206; 74/490.01, 74/490.6, 490.05; 901/30; 600/411, 424
See application file for complete search history.

(56) References Cited

U.S. PATENT DOCUMENTS

| | | | | |
|---|---|---|---|---|
| 1,149,762 | A | * | 8/1915 | Hendrickson .............. 403/63 X |
| 2,124,006 | A | * | 7/1938 | Parker ....................... 403/63 X |
| 4,805,477 | A | * | 2/1989 | Akeel ........................ 74/490.05 |
| 4,806,068 | A | * | 2/1989 | Kohli et al. .............. 74/479.01 |
| 5,853,328 | A | * | 12/1998 | Kobayashi et al. ...... 464/906 X |
| 5,916,328 | A | * | 6/1999 | Pritschow et al. ... 74/490.06 X |
| 6,497,548 | B1 | * | 12/2002 | Roy et al. ............ 74/490.06 X |

FOREIGN PATENT DOCUMENTS

FR            761431    *    3/1934    ................. 403/56
JP          61-201918    *    9/1986    ................. 384/206
SU            701793    *    12/1979    ................. 901/30

OTHER PUBLICATIONS

Class Definitions, Dec. 2000 ed., USPTO, p. 901-2.*
Chinzei, et al "MR Compatibility of Mechatronic Devices: Design Criteria", MICCAI, Sep. 1999, pp. 1020-1030.
Masamune, et al. "Development of an MRI-Compatible Needle Insertion Manipulator for Stereotatic Neurosurgery", Journal of Image Guided Surgery, 1995, pp. 242-248.
Schenck, et al. "Superconducting Open-Configuration MR. Imaging System for Image-Guided Therapy", Interventional Radiology, Jun. 1995, vol. 195, No. 3, pp. 805-816.
Chinzei, et al "MR Compatible Surgical Assist Robot: System Integration and Preliminary Feasibility Study," MICCAI 2000 Oct. 11-14 Lecture Notes in Computer Science vol. 1935 pp. 921-930, 2000.

* cited by examiner

*Primary Examiner*—Greg Binda
(74) *Attorney, Agent, or Firm*—Martin A. Farber

(57) ABSTRACT

A link mechanism to establish the position of a spherical bearing and the direction of an arm extending from the bearing is provided, which mechanism has a high precision of position and direction determination, does not require strong actuators, and is mechanically easy to accommodate MR compatibility, to be cleanable and to be sterilizable. The link mechanism has: an axial rod; and two spherical bearings to support the axial rod, the two spherical bearings being capable of changing relative positions, wherein the motion of one of the two spherical bearings relative to the axial rod along the axis is constrained, and the other of the spherical bearings can travel along the axial rod.

6 Claims, 4 Drawing Sheets

LINK MECHANISM OF SURGICAL ROBOT

BACKGROUND OF THE INVENTION a) Field of the Invention

The present invention is a link mechanism to determine a position and direction in three dimensional space. Such a link mechanism is applicable to determine the position and direction of a surgical assist apparatus, an end effector of a robot (manipulator) or the like.

b) Description of the Related Art

In MR/T (magnetic resonance and therapy), fusion of diagnosis and treatment, it is necessary that the presence and function of a medical equipment do not generate artifacts (such as noises and ghost) on the image. The mutual influence between a medical equipment and MRI is called MR compatibility.

Surgical assist robots are expected to be used in MR/T. However, since robot mechanism generally uses many metal components such as steel components, electromagnetic motors, electric sensors and the like, it has been difficult to realize MR compatibility. In particular, the end effector, which is used near to a patient, is required to have a very small magnetic susceptibility and low electrical noise radiation. It is therefore difficult to use a complicated mechanism, active mechanical elements such as motors, and various types of sensors.

Under such restrictions, surgical assist robot for MR/T must realize a mechanism to establish, for a robotic arm segment, at least the position (x y z orthogonal coordinates) and angles θ and φ (measured from the center of a coordinate axes system as, respectively, azimuth and elevation) to define the direction in three-dimensional space. It is also desired that the end effector is cleanable and sterilizable. The end effector is also required to be simple and compact so as not to interrupt the view field and the work area of the surgeon. In addition, the output power of an actuator should be as small as possible to maintain safety.

There are many conventional mechanisms to define the position (in terms of the coordinate axes x y z) and angles θ and φ. A typical example of such mechanisms is an arm type robot. The arm type robot uses a number of arm links interconnected by joints.

The arm type robot usually has actuators at the joints, otherwise it employs wire mechanism, shaft, and so on to transmit the driving power. The actuator makes it difficult to maintain MR compatibility, and inhibits cleaning and sterilization unless a water-proof process is performed strictly. Since the transmission mechanism is composed from many parts and is mechanically complicated, it requires a number of power transmission components so that it is mechanically complicated and a power loss cannot be neglected.

A parallel link mechanism, typically a hexa pod type robot, can be designed to place actuators remotely from the end effector. However, since links are concentrated near to, or at the end effector, the mechanical structure is complicated.

By designing the end effector to be lengthy, it may be MR compatible, cleanable and sterilizable.

In this case, however, its precision is degraded and stronger actuators are required. Such an end effector can be complicated and bulky, and consequently interrupt the view field of the surgeons.

Under such circumstances, a link mechanism to determine the position and angles has long been desired, which mechanism has a high precision of position and angle determination, does not require strong actuators, and is mechanically simple for enabling MR compatibility, cleaning and sterilization.

SUMMARY OF THE INVENTION

The invention has been made to accommodate such circumstances. The object of the present invention is to realize a link mechanism for determining the position and angles for an actuator, which mechanism has a high precision of position and angle determination, does not require strong actuators, and is mechanically simple to accommodate MR compatibility, cleaning and sterilization, and in which an end effector does not interrupt the field of view of the surgeon.

To achieve the above object, the invented link mechanism has the following features: an axial rod; and two spherical bearings to support the axial rod, the two spherical bearings being capable of changing positions of the links of the mechanism, wherein the motion of one of the two spherical bearings relative to the axial rod along the axis of the rod R is constrained, and the other of the two spherical bearings can travel along the axial rod R.

DETAILED DESCRIPTION OF THE PREFERRED EMBODIMENTS

An embodiment of the invention will be described with reference to the accompanying drawings.

Figure 1:
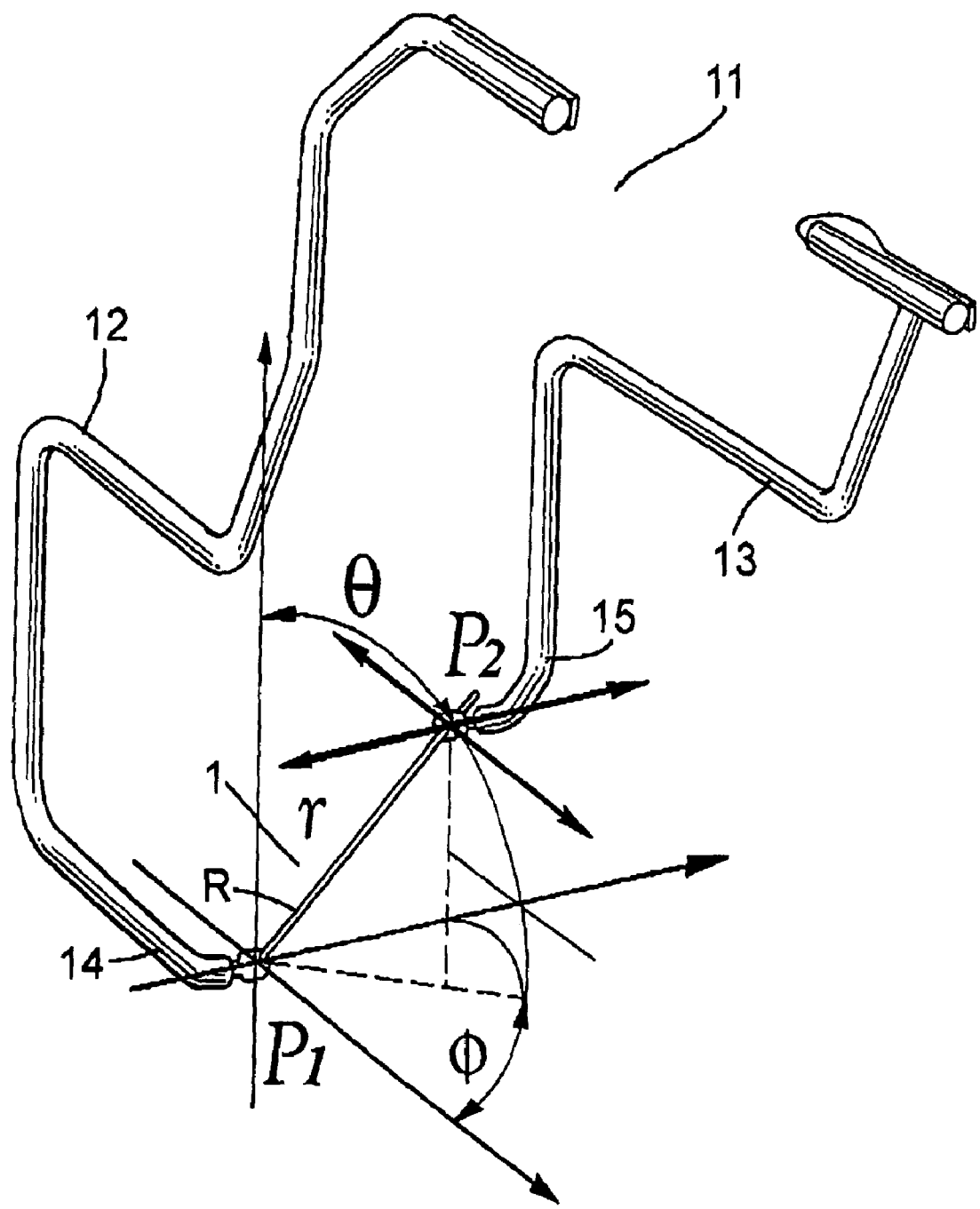
FIG. 1 is a perspective view of an implementation of an end effector of a robot, in accordance with a link mechanism based on this invention.

In FIG. 1, reference numeral 11 generally represents a robot end effector. A link mechanism of the invention is assembled in this robot end effector 11. The end effector 11 has a pair of elongated arms 12 and 13. This pair of arms 12 and 13 cooperatively maneuver to work on a subject. The base portion 14 of the arm 12 is fixed to the outer wheel 3(1) or the inner wheel 2(1), shown in FIGS. 2 and 3, of the spherical bearing $P_1$ of the link mechanism 1 of this invention to be described later, whereas the base portion 15 of the other arm 13 is fixed to the outer wheel 3(2) or the inner wheel 2(2) of the spherical bearing $P_2$.

Figure 2:
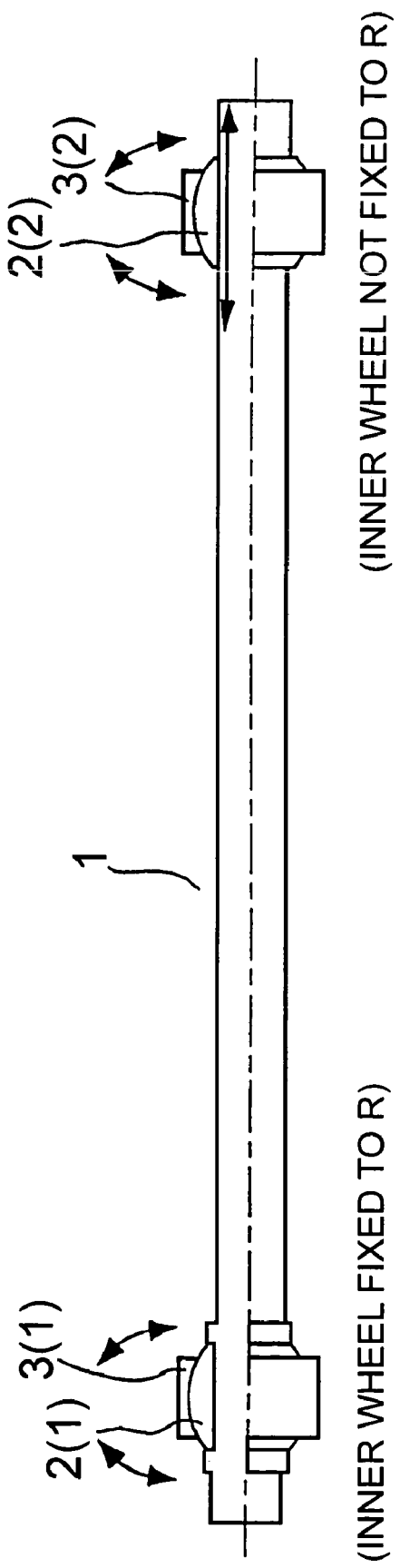
FIG. 2 is a front view of the link mechanism of the embodiment.
Figure 3:
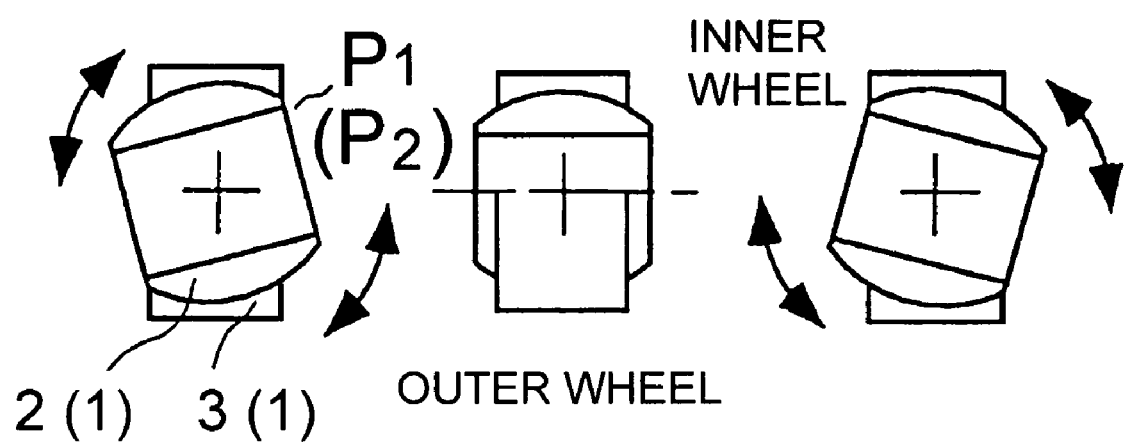
FIG. 3 is a diagram illustrating the motion of spherical bearings.

As shown in FIGS. 1, 2 and 3, the link mechanism 1 of this invention is composed of two spherical bearings $P_1$ and $P_2$ and an axial rod R which is a rigid element interconnecting the spherical bearings $P_1$ and $P_2$.

The spherical bearing $P_1$ travels in three dimensional space (or in a partial space thereof), whereas the position of the spherical bearing $P_2$ is constrained in three dimensional space or in a two-dimensional plane (or in a partial space or plane thereof) relative to the spherical bearing $P_1$.

Each of the spherical bearings $P_1$ and $P_2$ is composed of the inner wheel 2(1), 2(2) respectively and the outer wheel 3(1), 3(2) respectively. The inner and outer wheels 2(1) and 3(1) of the bearing $P_1$, and similarly for the bearing $P_2$, share a common centroid so that they rotate relative to each other around this point. It is a common specification of widely available spherical bearings. The axial rod R is fixed to the inner wheel 2(1) or outer wheel 3(1) of the spherical bearing $P_1$ which wheel is not fixed to the arm 12. The axial rod R is fixed neither to the inner wheel 2(2) nor to the outer wheel 3(2) of the spherical bearing $P_2$. The spherical bearing $P_2$ can therefore slide along the axial rod R as $P_2$ moves.

This link mechanism 1 can be made of only passive mechanical elements. Although sensors are not essential to determine the position and angles, such sensors may be used.

The spherical bearings $P_1$ and $P_2$ are driven by drivers (not shown). Such drivers and a method of determining the positions of the spherical bearings $P_1$ and $P_2$ may be any desired drivers and method.

The determination of the position and direction of the axial rod R of the link mechanism 1 constructed as above is accomplished as follows.

The representative three-dimensional coordinate (x y z) of the whole link mechanism 1 is defined by the position of the spherical bearing $P_1$, and at the same time, the direction (angles θ and φ of the axial rod R is determined from a motion of the spherical bearing $P_2$ relative to the spherical bearing $P_1$.

As the spherical bearing $P_2$ is driven, it has a relative displacement along of the axial rod R. To allow this displacement, it is necessary that the spherical bearing $P_2$ can slide along the axial rod R.

Figure 4:
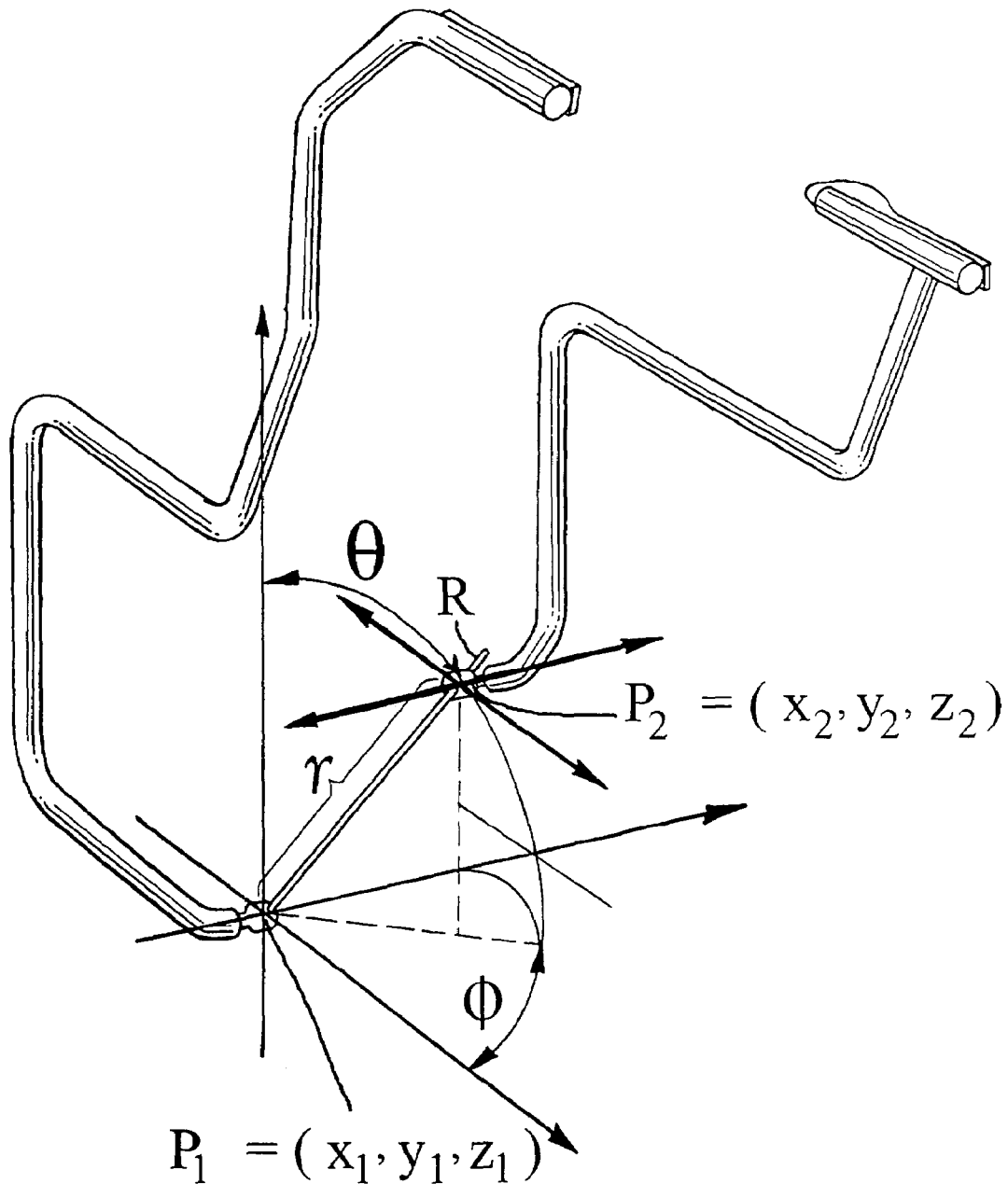
FIG. 4 is a diagram showing a relation among the positions and directions of spherical bearings $P_1$ and $P_2$ and an axial rod R.

FIG. 4 is a diagram showing relation of the spherical bearings $P_1$, $P_2$ and the axial rod R in terms of their position and direction. The angles φ and θ of the polar coordinate system satisfy the following equations:

$$x' = r \cos \phi \sin \theta$$

$$y' = r \sin \phi \sin \theta$$

$$z' = r \cos \theta$$

where $$x' = x_2 - x_1$$

$$y' = y_2 - y_1$$

$$z' = z_2 - z_1$$

$$r^2 = x'^2 + y'^2 + z'^2$$

wherein
r: distance between $P_1$ and $P_2$ on the axis R
$x_2$: coordinate value of $P_2$ on the x axis of xyz coordinate
$y_2$: coordinate value of $P_2$ on the y axis of xyz coordinate
$z_2$: coordinate value of $P_2$ on the z axis of xyz coordinate
$x_1$: coordinate value of $P_1$ on the x axis of xyz coordinate
$y_1$: coordinate value of $P_1$ on the y axis of xyz coordinate
$z_1$: coordinate value of $P_1$ on the z axis of xyz coordinate
θ: angle of R measured from x axis of x-z plane
φ: angle of R measured from y axis of y-z plane The length of the axial rod R should be longer than the maximum length of r.

In practice, the width of the spherical bearings $P_1$ and $P_2$ along the axial direction is additionally required. If r becomes longer than the length of the axial rod R, the spherical bearing $P_2$ is dismounted from the axial rod R.

The link mechanism of this invention can be composed from substantially only two spherical bearings and one axial rod. These components can be made of paramagnetic material having small magnetic susceptibility, such as ceramics, glass fiber reinforced material, carbon fiber reinforced material, wood, and non-ferrous metal. Active mechanical elements and sensors are not essential. This link mechanism has excellent characteristics in MR compatibility, and is readily detachable, cleanable and sterilizable.

The invention claimed is:

1. A link mechanism for a surgical assist robot to determine a position and direction of an axial rod, comprising:
    an axial rod; and
    two spherical bearings to support said axial rod, said two spherical bearings being capable of changing positions,
    wherein a motion of one of said two spherical bearings relative to said axial rod along an axis of said axial rod is constrained, and the other of said spherical bearings can travel along said rod; and
    wherein said rod and each of said spherical bearings constructed of material drawn from a class of paramagnetic materials of small magnetic susceptibility including ceramic material, glass fiber-reinforced material, carbon fiber reinforced material, wood, and non-ferrous metal, said material permitting use of the robot for magnetic resonance and therapy applications in an environment of an electromagnetic field without generation of artifacts in images produced by magnetic resonance and therapy applications.

2. A link mechanism for a surgical assist robot to determine a position and a direction of an axial rod, comprising:
    an axial rod; and
    two supports to support said axial rod, said two supports being capable of changing positions,
    wherein a motion of one of said two supports relative to said axial rod along an axis of said axial rod is constrained, and the other of said supports can travel along said axial rod; and
    wherein said rod and each of said spherical bearings constructed of material drawn from a class of paramagnetic materials of small magnetic susceptibility including ceramic material, glass fiber-reinforced material, carbon fiber reinforced material, wood, and non-ferrous metal, said material permitting use of the robot for magnetic resonance and therapy applications in an environment of an electromagnetic field without generation of artifacts in images produced by magnetic resonance and therapy applications.

3. A link mechanism for a surgical assist robot to determine a position and direction of an axial rod of robotic equipment, the link mechanism serving to direct a manipulator of a robot to determine the position and direction of a surgical assist apparatus in the presence of an electromagnetic field of magnetic resonance and therapy equipment, wherein the manipulator has a configuration to minimize magnetic susceptibility and electrical noise radiation, the link mechanism comprising:
    an axial rod; and
    two spherical bearings engaging with said axial rod, a second bearing of said two spherical bearings being capable of changing positions relative to a first bearing of said two spherical bearings along said axial rod, wherein said robot has a first manipulator extending from said first of said spherical bearings and a second manipulator extending from said second of said spherical bearings to engage the surgical assist apparatus while minimizing interaction with said electromagnetic field; and
    wherein a motion of said first spherical bearing relative to said axial rod along an axis of said axial rod is constrained, and said second spherical bearing can travel along said rod to enable a drive mechanism of the robot to position and to direct each of said first and said second manipulators; and wherein said rod and each of said spherical bearings constructed of material drawn from a class of paramagnetic materials of small magnetic susceptibility including ceramic material, glass fiber-reinforced material, carbon fiber reinforced material, wood, and non-ferrous metal, said material permitting use of the robot for magnetic resonance and therapy applications in an environment of an electromagnetic field without generation of artifacts in images produced by magnetic resonance and therapy applications.

4. A link mechanism for a surgical assist robot to determine a position having coordinates $(X_1, Y_1, Z_1)$ and a direction having coordinates $(\theta, \phi)$ of an axial rod (R) for robotic equipment works in the robotic workspace, the link mechanism comprising:

an axial rod (R); and first and second spherical bearings ($P_1$ and $P_2$) engaging with said axial rod (R), said first spherical bearing ($P_1$) having said position coordinates $(X_1, Y_1, Z_1)$, and said second spherical bearing ($P_2$) being capable of changing its position identified by coordinates (x', y', z') derived from an equation (1) relative to said first spherical bearing ($P_1$) along said axial rod (R), wherein $x' = r \cos \phi \sin \theta$ $y' = r \sin \phi \sin \theta$ $z' = r \cos \theta$     (1)

wherein said first spherical bearing ($P_1$) is capable of being driven to change the position of the rod in three-dimensional space by a driver and said second spherical bearing ($P_2$) is capable of being driven to change the position in three dimensional space or a two dimensional plane relative to said first spherical bearing ($P_1$) by a driver, said robot has said robotic equipment mounted on said axial rod (R); and the length of the axial rod (R) should be longer than the maximum length of r, and wherein a motion of said first spherical bearing ($P_1$) relative to said axial rod (R) along of said axial rod (R) is constrained, and said second spherical bearing ($P_2$) can travel along said axial rod (R) to enable a positioning and a directing of said axial rod (R) and said robotic equipment, wherein:

r: distance between $P_1$ and $P_2$ along the axis or axial rod (R)

$x_2$: coordinate value of $P_2$ along the x axis of xyz coordinate $y_2$: coordinate value of $P_2$ along the y axis of xyz coordinate $z_2$: coordinate value of $P_2$ along the z axis of xyz coordinate $x_1$: coordinate value of $P_1$ along the x axis of xyz coordinate $y_1$: coordinate value of $P_1$ along the y axis of xyz coordinate $z_1$: coordinate value of $P_1$ along the z axis of xyz coordinate $\theta$: angle of R measured from x axis of x-z plane $\phi$: angle of R measured from y axis of y-z plane $x' = x_2 - x_1$ $y' = y_2 - y_1$ $z' = z_2 - z_1$ $r^2 = x'^2 + y'^2 + z'^2$; and wherein said rod and each of said spherical bearings constructed of material drawn from a class of paramagnetic materials of small magnetic susceptibility including ceramic material, glass fiber-reinforced material, carbon fiber reinforced material, wood, and non-ferrous metal, said material permitting use of the robot for magnetic resonance and therapy applications in an environment of an electromagnetic field without generation of artifacts in images produced by magnetic resonance and therapy applications.

5. A link mechanism for a surgical assist robot to determine a position having coordinates $(X_1, Y_1, Z_1)$ and a direction having coordinates $(\theta, \phi)$ of an axial rod (R) for robotic equipment works in the robotic workspace, the link mechanism comprising:

an axial rod (R); and first and second supports ($P_1$ and $P_2$) engaging with said axial rod (R), said first support ($P_1$) having said position coordinates $(X_1, Y_1, Z_1)$ and said second support ($P_2$) being capable of changing its position identified by coordinates (x', y', z') derived from an equation (1) relative to said first support ($P_1$) along said axial rod (R), wherein $x' = r \cos \phi \sin \theta$ $y' = r \sin \phi \sin \theta$ $z' = r \cos \theta$     (1)

wherein said first support ($P_1$) is capable of being driven to change the position of the rod in three-dimensional space by a driver and said second support ($P_2$) is capable of being driven to change the position in three dimensional space or a two dimensional plane relative to said first support ($P_1$) by a driver, said robot has said robotic equipment mounted on said axial rod (R); and the length of the axial rod (R) should be longer than the maximum length of r, and wherein a motion of said first support ($P_1$) relative to said axial rod (R) along of said axial rod (R) is constrained, and said second support ($P_2$) can travel along said axial rod (R) to enable a positioning and a directing of said axial rod (R) and said robotic equipment, Wherein:

r: distance between $P_1$ and $P_2$ along the axis or axial rod (R)

$x_2$: coordinate value of $P_2$ along the x axis of xyz coordinate $y_2$: coordinate value of $P_2$ along the y axis of xyz coordinate $z_2$: coordinate value of $P_2$ along the z axis of xyz coordinate $x_1$: coordinate value of $P_1$ along the x axis of xyz coordinate $y_1$: coordinate value of $P_1$ along the y axis of xyz coordinate $z_1$: coordinate value of $P_1$ along the z axis of xyz coordinate $\theta$: angle of R measured from x axis of x-z plane $\phi$: angle of R measured from y axis of y-z plane $x' = x_2 - x_1$ $y' = y_2 - y_1$ $z' = z_2 - z_1$ $r^2 = x'^2 + y'^2 + z'^2$; and wherein said rod and each of said spherical bearings constructed of material drawn from a class of paramagnetic materials of small magnetic susceptibility including ceramic material, glass fiber-reinforced material, carbon fiber reinforced material, wood, and non-ferrous metal, said material permitting use of the robot for magnetic resonance and therapy applications in an environment of an electromagnetic field without generation of artifacts in images produced by magnetic resonance and therapy applications.

6. Robotic apparatus comprising a link mechanism with a first manipulator and a second manipulator connected to the link mechanism to determine the position and direction of a surgical assist apparatus in the presence of an electromagnetic field of magnetic resonance and therapy equipment, the link mechanism comprising:

an axial rod; and two spherical bearings engaging with said axial rod, a second bearing of said two spherical bearings being capable of changing positions relative to a first bearing of said two spherical bearings along said axial rod, wherein said first manipulator extends from said first of said spherical bearings and said second manipulator extends from said second of said spherical bearings to engage the surgical assist apparatus while minimizing interaction with said electromagnetic field; and wherein a motion of said first spherical bearing relative to said axial rod along an axis of said axial rod is constrained, and said second spherical bearing can travel along said rod to enable a drive mechanism to position and to direct each of said first and said second manipulators; and wherein said rod and each of said spherical bearings constructed of material drawn from a class of paramagnetic materials of small magnetic susceptibility including ceramic material, glass fiber-reinforced material, carbon fiber reinforced material, wood, and non-ferrous metal, said material permitting the use of the robot for magnetic resonance and therapy applications in an environment of an electromagnetic field without generation of artifacts in images produced by magnetic resonance and therapy applications.

* * * * *